United States Patent [19]
Fujiwara et al.

[11] Patent Number: 5,681,802
[45] Date of Patent: Oct. 28, 1997

[54] MILD ANTIMICROBIAL LIQUID CLEANSING FORMULATIONS COMPRISING BUFFERING COMPOUND OR COMPOUNDS AS POTENTIATOR OF ANTIMICROBIAL EFFECTIVENESS

[75] Inventors: Mitsuko Fujiwara, Edgewater; Carol Vincent, Wanaque, both of N.J.; Kavssery Ananthapadmanabhan, New Windsor, N.Y.; Virgilio Villa, Bergenfield, N.J.

[73] Assignee: Lever Brothers Company, Division of Conopco, Inc., New York, N.Y.

[21] Appl. No.: 252,298

[22] Filed: Jun. 1, 1994

[51] Int. Cl.$^6$ .................... C11D 3/20; C11D 1/94
[52] U.S. Cl. ............ 510/130; 510/131; 510/159; 510/383; 510/405; 510/428; 510/433; 510/488
[58] Field of Search .................... 252/106, 108, 252/121, 551, 142, 173, DIG. 5; 510/130, 131, 159, 383, 405, 428, 433, 488

[56] References Cited

U.S. PATENT DOCUMENTS

| | | | |
|---|---|---|---|
| 3,218,260 | 11/1965 | Lewandowski | 252/142 |
| 4,002,775 | 1/1977 | Kabara | 426/532 |
| 4,147,782 | 4/1979 | Klein et al. | 424/230 |
| 4,406,884 | 9/1983 | Fawzi et al. | 424/81 |
| 4,997,851 | 3/1991 | Isaacs et al. | 514/558 |
| 5,002,680 | 3/1991 | Schmidt et al. | 252/90 |
| 5,011,681 | 4/1991 | Ciotti et al. | 424/81 |
| 5,132,037 | 7/1992 | Greene et al. | 252/108 |
| 5,137,715 | 8/1992 | Hoshowski et al. | 424/70 |
| 5,186,855 | 2/1993 | Crudden | 252/117 |
| 5,227,086 | 7/1993 | Kacher et al. | 252/112 |
| 5,234,619 | 8/1993 | Greene et al. | 252/108 |
| 5,300,249 | 4/1994 | Schwartz et al. | 252/108 |
| 5,308,526 | 5/1994 | Dias et al. | 252/125 |
| 5,372,751 | 12/1994 | Rys-Cicciari et al. | 252/554 |
| 5,378,731 | 1/1995 | Andrews et al. | 514/552 |
| 5,409,640 | 4/1995 | Giret et al. | 252/546 |
| 5,422,280 | 6/1995 | Helliwell et al. | 436/72 |
| 5,429,815 | 7/1995 | Faryniarz et al. | 424/47 |

FOREIGN PATENT DOCUMENTS

| | | |
|---|---|---|
| 0024031 | 2/1981 | European Pat. Off. . |
| 0037224 | 10/1981 | European Pat. Off. . |
| 0193386 | 9/1986 | European Pat. Off. . |
| 244144 | 11/1987 | European Pat. Off. . |
| 488606 | 6/1992 | European Pat. Off. . |
| 0570794 | 11/1993 | European Pat. Off. . |
| 0573329 | 12/1993 | European Pat. Off. . |
| 2223049 | 10/1974 | France . |
| 2128627 | 5/1984 | United Kingdom . |
| 91/09923 | 7/1991 | WIPO . |
| 92/18100 | 10/1992 | WIPO . |
| 94/18292 | 8/1994 | WIPO . |

OTHER PUBLICATIONS

Kabara, "Antimicrobial Agents Derived from Fatty Acids", JAOCS, 61(2):Feb. 1984.

Shellow, "pHresh 3.5: A New Low pH Liquid Skin Cleanser", The Journal of International Medical Research (1981) vol. 9, pp. 297–299.

*Primary Examiner*—Paul Lieberman
*Assistant Examiner*—Lorna M. Douyon
*Attorney, Agent, or Firm*—Ronald A. Koatz

[57] ABSTRACT

A liquid skin cleansing composition comprises (1) mild surfactant systems; (2) 0.1 to 10% by wt. of a compound or compounds which buffer the pH of the composition; and (3) 1% to 99% water to potentiate the bactericidal activity. In a second embodiment of the invention, the buffering compound or compounds potentiates antibacterial effect in compositions already containing an antibacterial agent.

6 Claims, 4 Drawing Sheets

MILD ANTIMICROBIAL LIQUID CLEANSING FORMULATIONS COMPRISING BUFFERING COMPOUND OR COMPOUNDS AS POTENTIATOR OF ANTIMICROBIAL EFFECTIVENESS

BACKGROUND OF THE INVENTION

The present invention relates to liquid cleansing compositions having enhanced antimicrobial effectiveness. More specifically, the invention relates to a compound or compounds which potentiate the antibacterial activity of liquid cleaning formulations by buffering the pH of the formulation such that the pH will rise no higher than 5.5, preferably between 2.5 to 5.0 under in use conditions (as opposed to initial pH).

There is a large demand in the market for mild liquid cleansing formulations which additionally have an antibacterial effect. Antibacterial cleansers are preferred because they kill germs and mild personal cleansers are preferred to minimize skin irritation, dryness, etc. However, the combination of mild cleansing formulations and strong antibacterial effect is difficult to achieve. Thus, for example, while soaps provide antibacterial effects, they are not mild to the skin. When very mild non-soap surfactants are used, antibacterial effect is greatly compromised.

The balancing act between providing mildness and effective antibacterial effectiveness is recognized for example in International Publication WO 92/18100. In this publication, improved clinical mildness is said to be provided through the use of a water soluble cationic polymer (see page 10, lines 24–29). Cationic polymer is apparently used instead of additional ethoxylated surfactant because the percent of ethoxylated mildness surfactant must be minimized in order not to affect antibacterial effectiveness (page 7, lines 4–6).

Another approach to providing mildness effect without affecting antibacterial properties is that which appears to be used by Dial in, for example, Liquid Dial Plus with Moisturizers Antibacterial Soap®. Here, mildness benefits are apparently provided by the use of moisturizing compounds rather than by the use of very mild surfactants alone (which, as indicated above, compromises antibacterial effectiveness).

In both cases, it can be readily seen that it is extremely difficult to provide effective antibacterial action in the presence of very mild surfactants. Rather, it is necessary to minimize the presence of those mild surfactants, to use larger amounts of harsher suffactants or soaps and to mask the effects of the harshness by providing cationic mildness conditioning agents (WO 92/18100) or moisturizers (as in the Dial product).

It would be greatly beneficial if antibacterial effectiveness could be provided either by providing a compound or compounds which alone or together buffer pH of a liquid composition at a pH low enough to provide antibacterial effectiveness for that composition formulation; or by providing a compound or compounds which alone or together buffer pH of a liquid composition containing anti-bacterial agent thereby enhancing (i.e., potentiating) the effect of the antibacterial agent even in compositions with very mild surfactant systems.

Fatty acids and their ester derivatives have been used to provide antimicrobial effectiveness in foods, pharmaceuticals and cosmetics (see, for example EP 0,244,144; U.S. Pat. No. 4,002,775; U.S. Pat. No. 4,406,884; U.S. Pat. No. 4,997,851 and Kabara in JAOCS, vol. 61 No. 2, (February, 1984)).

The use of short chain fatty acids generally as potentiators of germicides is also known. These fatty acids, for example, have been used as potentiators with halogenated germicides at high pH and with isethiazolones (see FR 2,223,049 and EP 488,606).

U.S. Pat. No. 3,218,260 to Lewandowski discloses cleaner compositions containing various organic or inorganic acids. The pH of these compositions (less than 2) is well below the pH of the skin cleansing compositions of the present invention.

In none of these references is it taught or suggested that one or more compounds be used either to enhance antibacterial effect in liquid skin cleansing compositions or to potentiate antibacterial compounds which may already be present in liquid skin cleansing compositions at the pH specified by the claims of the subject invention.

U.S. Pat. No. 5,132,037 to Greene et al. teaches aqueous compositions in which $C_8$–$C_{22}$ free fatty acids may be used. All examples (palmitic, stearic) are clearly directed to longer chain fatty acids and there is absolutely no recognition of the antibacterial or potentiating effect of lower chain fatty acids.

Unexpectedly, applicants have now found that one or more compounds (e.g., short chained fatty acids, hydroxy acids and polymeric acids) may be used to buffer low pH within a defined low pH range and to therefore:

(1) enhance the antibacterial effect of liquid skin cleansing compositions; and/or (2) potentiate antimicrobial effect of liquid skin cleansing compositions which already contain an antimicrobial agent.

BRIEF SUMMARY OF THE INVENTION

The present invention relates to liquid skin cleansing compositions comprising:

(1) any mild surfactant system (i.e., any one or more surfactants which alone or together are demonstrated by clinical tests to be milder than soap itself) in an amount of from about 1–99% by wt., preferably 2–85% by wt., more preferably 3–40% by wt. surfactant system;

(2) 0.1 to 10%, preferably 0.1 to 5%, more preferably 0.5 to 5.0% by weight of a compound or compounds which alone or together buffer the pH of the liquid skin cleanser composition such that the pH is no higher than 5.5 under in-use conditions (i.e., 1:0.5 to 1:100 dilution, preferably 1:1 to 1:25 dilution of product in $H_2O$); and (3) 1% to 99% by wt., preferably 15 to 97%, most preferably 60 to 97% by wt. water.

In a second embodiment of the invention, the liquid skin cleansing composition comprises 0.001% to 5% by weight of an antibacterial agent and the buffering compound or compounds act to potentiate the antimicrobial effect of the composition.

DETAILED DESCRIPTION OF THE INVENTION

Figure 1:
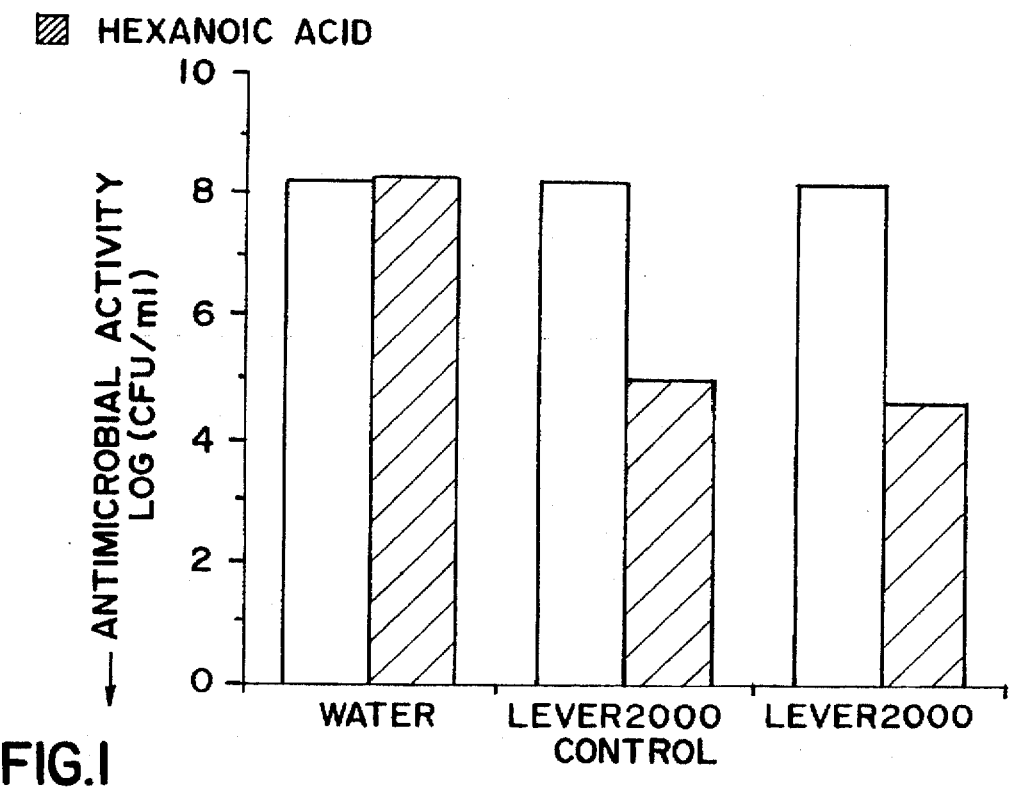
FIG. 1 shows the effect of short chain fatty acids on the antimicrobial activity of one of the skin cleansing formulations of the invention, both with and without antibacterial agent (e.g., Triclosan or DP300®).

The present invention relates to liquid skin cleansing compositions comprising 1 to 99% by weight, preferably 2 to 85%, more preferably 3 to 40% of a mild surfactant system comprising one or more surfactants which alone or together have been clinically tested to be milder than soap itself as measured by zein solubilization test (soap yields 80% zein solubilized). Preferably, the mildness is such that zein solubilization is in the range 10–60% solubilization.

A number of anionic, nonionic, cationic and amphoteric surfactants may be employed in the surfactant system of the invention provided of course that the surfactant, if used alone, or surfactant mixture is milder than would be soap itself as measured by the zein solubilization test.

Among suitable anionic co-actives are the alkyl ether sulfates, acyl isethionates, alkyl ether sulfonates, sarcosinates, sulfosuccinates, taurates and combinations thereof. Among suitable amphoteric co-actives may be included alkylbetaines, amidopropyl betaines, amidopropyl sultaines and combinations thereof.

Alkyl ether sulfates of the present invention will be of the general formula $R-(OCH_2CH_2)_nOSO_3-M^+$ wherein R ranges from $C_8-C_{20}$ alkyl, preferably $C_{12}-C_{15}$ alkyl, n is an integer from 1 to 40, preferably from 2 to 9, optimally about 3, and $M^+$ is a sodium, potassium, ammonium or triethanolammonium cation.

Typical commercial co-actives of this variety are listed in the Table below:

| Trademark | Chemical Name | Physical Form | Manufacturer |
| --- | --- | --- | --- |
| Steol CS 330 | Sodium Laureth Sulfate | Liquid | Stepan |
| Standopol ES-3 | Sodium Laureth Sulfate | Liquid | Henkel |
| Alkasurf ES-60 | Sodium Laureth Sulfate | Paste | Alkaril |
| Cycloryl TD | TEA Laureth Sulfate | Paste | Cyclo |
| Standapol 125-E | Sodium Laureth-12 Sulfate | Liquid | Henkel |
| Cedepal TD407MF | Sodium Trideceth Sulfate | Paste | Miranol |
| Standopol EA-2 | Ammonium Laureth Sulfate | Liquid | Henkel |

Alkyl ether sulfonates may also be employed for the present invention. Illustrative of this category is a commercial product known as Avenel S-150 commonly known as a sodium $C_{12}-C_{15}$ Pareth-15 sulfonate.

Another co-active type suitable for use in the present invention is that of the sulfosuccinates. This category is best represented by the monoalkyl sulfosuccinates having the formula $RO_2CCH_2CH(SO_3-Na^+)COO-M^+$; and amido-MEA sulfosuccinates of the formula: $RCONHCH_2CH_2O_2CCH_2CH(SO_3-M^+)COO-M^+$; wherein R ranges from $C_8-C_{20}$ alkyl, preferably $C_{12}-C_{15}$ alkyl and $M^+$ is a sodium, potassium, ammonium or triethanolammonium cation. Typical commercial products representative of these co-actives are those listed in the Table below:

| Trademark | Chemical Name | Physical Form | Manufacturer |
| --- | --- | --- | --- |
| Emcol 4400-1 | Disodium Lauryl Sulfosuccinate | Solid | Witco |
| Witco C5690 | Disodium Cocoamido MEA Sulfosuccinate | Liquid | Witco |
| McIntyre Mackanate CM40F | Disodium Cocoamido MEA Sulfosuccinate | Liquid | McIntyre |
| Schercopol CMSNa | Disodium Cocoamido MEA Sulfosuccinate | Liquid | Scher |
| Emcol 4100M | Disodium Myristamido MEA Sulfosuccinate | Paste | Witco |
| Schercopol | Disodium Oleamido MEA | Liquid | Scher |
| Varsulf S13333 | Disodium Ricionoleamido MEA Sulfosuccinate | Solid | Scherex |

Sarcosinates may also be useful in the present invention as a co-active. This category is indicated by the general formula $RCON(CH_3)CH_2CO_2-M^+$, wherein R ranges from $C_8-C_{20}$ alkyl, preferably $C_{12}-C_{15}$ alkyl and $M^+$ is a sodium, potassium ammonium or triethanolammonium cation. Typical commercial products representative of these co-actives are those listed in the Table below:

| Trademark | Chemical Name | Physical Form | Manufacturer |
| --- | --- | --- | --- |
| Hamposyl L-95 | Sodium Lauroyl Sarcosinate | Solid | W. R. Grace |
| Hamposyl TOC-30 | TEA Cocoyl/Sarcosinate | Liquid | W. R. Grace |

Taurates may also be employed in the present invention as co-actives. These materials are generally identified by the formula $RCONR'CH_2CH_2SO_3-M^+$, wherein R ranges from $C_8-C_{20}$ alkyl, preferably $C_{12}-C_{15}$ alkyl, R' ranges from $C_1-C_4$ alkyl, and $M^+$ is a sodium, potassium, ammonium or triethanolammonium cation. Typical commercial products representative of these co-actives are those listed in the Table below:

| Trademark | Chemical Name | Physical Form | Manufacturer |
| --- | --- | --- | --- |
| Igepon TC 42 | Sodium Methyl Cocoyl Taurate | Paste | GAF |
| Igepon T-77 | Sodium Methyl Oleoyl Taurate | Paste | GAF |

Within the category of amphoterics there are three general categories suitable for the present invention. These include alkylbetaines of the formula $RN^+(CH_3)_2CH_2CO_2-M^+$, amidopropyl betaines of the formula $RCONHCH_2CH_2CH_2N^+(CH_3)_2CH_2CO_2-M^+$, and amidopropyl sultaines of the formula $RCONHCH_2CH_2N^+(CH_3)_2CH_2SO_3-M^+$ wherein R ranges from $C_8-C_{20}$ alkyl, preferably $C_{12}-C_{15}$ alkyl, and $M^+$ is a sodium, potassium, ammonium or triethanolammonium cation. Typical commercial products representative of these co-actives are found in the Table below:

| Trademark | Chemical Name | Physical Form | Manufacturer |
|---|---|---|---|
| Tegobetaine F | Cocamidopropyl Betaine | Liquid | Goldschmidt |
| Lonzaine C | Cocamidopropyl Betaine | Liquid | Lonza |
| Lonzaine CS | Cocamidopropyl Hydroxysultaine | Liquid | Lonza |
| Lonzaine 12C | Coco-Betaine | Liquid | Lonza |
| Schercotaine MAB | Myristamido-propyl Betaine | Liquid | Lonza |
| Velvetex OLB-50 | Oleyl Betaine | Paste | Henkel |

Within the broad category of liquid actives, the most effective are the alkyl sulfates, alkyl ether sulfates, alkyl ether sulfonates, sulfosuccinates, and amidopropyl betaines.

Another preferred surfactant is an acyl isethionate having the formula

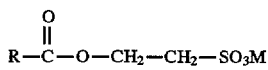

in which R denotes a linear or branched alkyl group and M denotes an alkali metal or alkaline earth metal or an amine.

Another surfactant which may be used are the monoalkyl or dialkylphosphate surfactants.

Another mild surfactant which may be used, preferably used as primary surfactant in combination with other surfactants noted above, is sodium coco glyceryl ether sulfonate. While desirable to use because of its mildness properties, this coco AGS alone does not provide optimum lather creaminess. A sodium 90/10 coconut/tallow alkyl AGS distribution is preferred for creaminess. Salts other than the sodium salt such as TEA-, ammonium, and K-AGS and chain length distributions other than 90/10 coconut/tallow are usable at moderate levels. Also, some soap may be added to improve lather volume and speed of lathering. Certain secondary co-surfactants used in combination with AGS can also provide a creamier and more stable lather. These secondary surfactants should also be intrinsically mild. One secondary surfactant that has been found to be especially desirable is sodium lauroyl sarcosinate (trade name Hamposyl L, made by Hampshire Chemical).

The amphoteric betaines and sultaines noted above can be used as the sole surfactant, but are more preferred as a co-surfactant. Nonionics generally should not be used as the sole surfactant in this product if high forming is desirable; however, they can be incorporated as a co-surfactant.

Nonionic and cationic surfactants which may be used include any one of those described in U.S. Pat. No. 3,761,418 to Parran, Jr., hereby incorporated by reference into the subject application.

Soaps can be used at levels of about 1–10%. Soaps can be used at higher level provided that the surfactant mixture is milder than soap. The soaps may be added neat or made in situ via adding a base, e.g., NaOH; to convert free fatty acids.

Of course, as noted above, soaps should only be used as cosurfactants to the extent that the surfactant system is milder than soap alone.

A preferred surfactant active system is one such that acyl isethionate comprises 1 to 15% by weight of the total composition, an anionic other than acyl isethionate (e.g., ammonium lauryl ether sulfate) comprises 1 to 15% by weight of the total composition and amphoteric comprises 0.5 to 15% by weight of the total composition.

SUFFERING COMPONENT

The second critical component of the liquid compositions of the invention is the compound or compounds which alone or together buffer the pH of the formulation under in-use condition such that the pH is from about 2.5 to 5.5, preferably 3.5 to 5.0.

By in-use is meant dilution of 1:0.5 to 1:100, preferably 1:1 to 1:25 of the product in water during use.

This compound or compounds can be any organic acid or its anhydride (including polymeric organic acids or anhydrides) or inorganic acid which lowers pH of the compositions in use to 2.5 to 5.5 and buffers at this pH.

Examples of inorganic acids which may lower pH and buffer at this pH are phosphoric acid or carbonic acid. Examples of organic acids and their anhydrides include carboxylic acids, hydroxy carboxylic acids and polymeric acids such as polyacrylic acids, polymethacrylic acids, pectic acids, etc.

Preferred organic compounds buffering at low pH are short chain fatty acids. The fatty acid may be a substituted or unsubstituted, saturated or unsaturated fatty acids having a chain length of $C_2$–$C_{18}$, preferably $C_4$–$C_{10}$. While not wishing to be bound by theory, it is believed that longer chain lengths function better with increased solubility (e.g., higher substitution). In general, however, lower chain lengths are preferred. The fatty acid will generally comprise about 0.1% to 10% by weight of the composition.

Another class of organic acid which may be used are the hydroxy carboxylic acids. This includes any organic compound having at least one carboxylic acid group and at least one hydroxyl group. Preferably, the chain length of the acid should be $C_2$ to $C_{18}$, more preferably $C_2$ to $C_{12}$. Among the many acids which may be used include citric acid, lactic acid, glycolic acid, α-hydroxy $C_8$ acid, α-hydroxy $C_{16}$ acid, acylated citric acid and β-hydroxybutyric acid.

Polymeric acids or their anhydrides which may be used according to this invention are selected from the group of polymer containing carboxylic acids or anhydrides with weight average molecular weight of at least 3,000 and mole % carboxyl functionality of at least 40%.

In a second embodiment of the invention, the liquid skin cleansing compositions of the subject invention must contain an antibacterial agent. In this embodiment of the invention, the buffering compound or compounds described above not only may provide antibacterial effect on its own, but also enhances (potentiates) the antibacterial effectiveness of the antibacterial agent.

The antibacterial agent can be present at a level of from about 0.001% to about 5%, typically from about 0.01% to about 2%, and preferably from about 0.01% to about 1.5% by weight of the composition. The level is selected to provide the desired level of antibacterial activity and can be modified as desired. The preferred antibacterial agent is 2-hydroxy-4,2',4'-trichlorodiphenylether (DP300). Other antibacterial agents are set out below. Many antibacterial agents, known to those skilled in the art and disclosed in e.g., U.S. Pat. Nos. 3,835,057 and 4,714,563, both incorporated hereinbefore by reference, may be used.

Antimicrobials

Suitable antibacterial agents which may be used in the subject invention (i.e., in one embodiment of the invention) include:

2-hydroxy-4.2',4'-trichlorodiphenylether (DP300);
2,6-dimethyl-4-hydroxychlorobenzene (PCMX);
3,4,4'-trichlorocarbanilide (TCC);
3-trifluoromethyl-4,4'-dichlorocarbanilide (TFC);
2,2'-dihydroxy-3,3',5,5',6,6'-hexachlorodiphenylmethane;
2,2'-dihydroxy-3,3',5,5'-tetrachlorodiphenylmethane;
2,2'-dihydroxy-3,3',dibromo-5,5'-dichlorodiphenylmethane;
2-hydroxy-4,4'-dichlorodiphenylether;
2-hydroxy-3,5',4-tribromodiphenlylether; and
1-hydroxyl-4-methyl-6-(2,4,4-trimethylpentyl)-2(1 H)-pyridinone (Octopirox).

Other suitable antimicrobials include:
Benzalkonium chloride
Benzethonium chloride
Carbolic acid
Cloflucarbon (Irgasan CF3;4,4'-dichloro-3-(trifluoromethyl) carbanilide)
Chlorhexidine (CHX; 1,6-di(4'-chlorophenyl-diguanido) hexane)
Cresylic acid
Hexetidine (5-amino-1,3-bis(2-ethylhexyl)-5-methylhexahydropyrimidine)
Iodophors
Methylbenzethonium chloride
Povidone-iodine
Tetramethylthiuram disulfide (TMTD; Thiram)
Tribrominated salicylanilide In addition to a mild surfactant compound or compounds; the pH buffering compound or compounds; water; and optionally (or as required in one embodiment), antimicrobial agent, the liquid skin cleansing compositions may contain optionals as described below.

Each of the above components can be incorporated in an aqueous vehicle which may, in addition, include such materials as organic solvents, such as ethanol; thickeners, such as carboxymethylcellulose, magnesium aluminum silicate, hydroxyethylcellulose, methylcellulose or carbopols; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The following preservatives may also be used in the liquid skin cleansers of the invention

LIQUID SKIN CLEANSER PRESERVATIVES

| PRESERVATIVE | CHEMICAL NAME |
|---|---|
| Bronopol | 2-Bromo-2nitropropane-1,3,diol |
| Dowicil 200 | cis Isomer of 1-(3-chloroallyl)-3,5,7-triaza-1-azoniaadamantane-chloride OR Quaternium 15 |
| Glycacil | 3-Iodo-2-propynyl butyl carbamate |
| Glydant XL 1000 | DMDM Hydantoin OR dimethyloldimethylhydantoin |
| Glydant Plus | DMDM Hydantoin and 3-iodo-2-propynyl butyl carbamate |
| Formaldehyde | Formaldehyde |
| Germall II | N-(Hydroxymethyl)-N-(1,3-dihydroxymethyl-2,5-dioxo-4-imidazolidinyl)-N'-(hydroxymethyl) urea OR Diazolidinyl urea |
| Germall 115 | N,N'-methylene-bis-[N'-1-(hydroxymethyl)-2,5-dioxo-4-imidazolidinyl]urea OR imidazolidinyl urea |
| Glutaraldehyde | Glutaraldehyde |
| Kathon CG | Mixture of 5-chloro-2-methyl-4-isothiazoline-3-one- and 2-methyl-4-isothiazoline-3-one OR Mixture of methyl, chloromethyl isothiazolinone, and methyl isothiazolinone |
| Parabens | Methyl Paraben, and Ethyl Paraben, and Propyl Paraben and Butyl Paraben OR those esters of p-hydroxybenzoic acid |
| Phenoxyethanol | 2-Phenoxyethanol |
| Salicylic Acid | Salicylic Acid OR o-Hydroxybenzoic acid |
| Sorbic Acid | Sorbic Acid, Potassium Sorbate |

Coconut acyl mono- or diethanol amides as suds boosters, and strongly ionizing salts such as sodium chloride and sodium sulfate may be used to advantage.

Antioxidants such as, for example, butylated hydroxytoluene (BHT) may be used advantageously in amounts of about 0.01% or higher if appropriate.

Cationic conditioners which may be used include Quatrisoft LM-200 (Polyquaternium-24); polyethylene glycols such as

| Polyox | WSR-205 | PEG 14M, |
| | WSR-N-60K | PEG 45M, or |
| | WSR-N-750 | PEG 7M; and |
| Merquat Plus 3330 - Polyquaternium 39. | | |

Thickeners which may be used include Americoll Polymer HM 1500 (Nonoxynyl Hydroethyl Cellulose); Glucan DOE 120 (PEG 120 Methyl Glucose Dioleate).

Unless stated otherwise, the percentages in the specification, examples and claims are percentages by weight.

The following examples are intended for illustrative purposes only and should not be construed to limit the invention in any way.

EXAMPLES

An In vitro Bactericidal Kill Test is used to measure antimicrobial activity in the examples which follow. Methodology for the test is set forth below:

In Vitro Bactericidal Kill Test

An in vitro bactericidal test was used to determine the antibacterial effect of products on Staphylococcus aureus ATCC #6538 during a short contact time. One milliliter (about $10^8$ cells) of bacteria was exposed for one minute to a one-percent solution of liquid skin cleansing composition. The sample was added to additional water, mixed, and further diluted in 0.1% peptone. Duplicate samples of appropriate dilutions were plated on neutralizing media. In addition, the bacterial culture was plated to determine the actual number of organisms inoculated. The plates were incubated at 34° C. for 48 hours and enumerated. The CFU/ml (colony forming units per milliliter) from dilutions with plate counts in the range of 30-300 were averaged together to produce the final CFU/ml.

The results may be expressed as the log of the CFU/ml. The culture control indicates the actual number of bacteria inoculated while the water control reflects the number of organisms recovered in the absence of product. The lower the number, the more effective the solution was in killing the bacteria.

In this assay, a sampling error of approximately 0.5 log is likely, therefore differences of 0.5 log between products may not be significant. As a result, the data should be viewed in terms of trends rather than as absolute numbers.

Example 1

Applicants tested the effect of 2% hexanoic acid in (1) water; (2) a full liquid skin cleansing formulation as set forth below containing no Triclosan (DP300); and (3) a full liquid skin cleansing formulation (also as set forth below) with Triclosan. The results are set forth in FIG. 1.

The formulation used was as follows:

| INGREDIENT | % BY WEIGHT |
| --- | --- |
| Acyl Isethionate | 1–15% |
| Anionic other than Acyl Isethionate (SLES)* | 1–15% |
| Amphoteric Surfactant** | 5–15% |
| pH Buffering Compound (Hexanoic Acid) | 1–5% |
| Sequestrant (EDTA or EHDP) | 0.01–0.1% |
| Moisturizer (e.g. cationic polymer) | 0.05–3.0% |
| Standard additives (e.g., dyes, perfumes) | 0–10% |
| Water | Balance |

*Sodium lauryl ether sulfate
**Cocamidopropyl betaine

As seen from FIG. 1, hexanoic acid increases antimicrobial activity in the full formulation both with and without Triclosan.

Example 2

Zein Solubilization Assay In vitro "Mildness" Test/ Assessing Mildness

It is generally believed that surfactants are irritants because they penetrate the stratum corneum and then react with the inner cells of the epidermis.

Traditionally, the study of percutaneous absorption has focused on measuring the diffusion of chemicals through the stratum corneum.

We have obtained information on mildness potentials of the compositions of the invention through the use of in vitro tests which have been demonstrated to correlate well with in vivo tests.

Gotte in Proc. Int. Cong. Surface Active Subs., 4th Brussels (1964), 3, 83–90 and Schwinger in Kolloid-Z.Z. Poly., (1969), 233, 898 have shown that the ability to solubilize zein, an insoluble maize protein, correlates well with irritation potential.

More specifically, the greater the zein solubilization, the greater the irritation potential of a composition.

In order to test irritancy potential, a 1% solution (by weight active) of surfactant (30 mls) was added to 1.5 g zein and stirred at room temperature for one hour. Residual zein was collected by centrifugation and dried under vacuum to constant weight. Differences between starting and residual weights were used to calculate % zein dissolved.

The zein dissolution values for some skin cleansing formulations generally compared to soap are given below:

Soap (Ivory®) 82.4%
Dove® Beauty Bar 55.0%
Liquid Lever 2000® 41.9%

Using the zein solubilation assay, the formulations of the invention all showed zein solubilization percentage well below that of soap. Specifically, the composition of Example 1 had solubility of about 28%. When octanoic acid was used, solubility was about 31%.

Example 3

In order to see the effect of chain length on the antibacterial effect of the compound or compounds of the invention, applicants tested various saturated and unsaturated $C_2$ to $C_{20}$ fatty acids to determine their effect. Results are set forth in FIG. 2.

Figure 2:
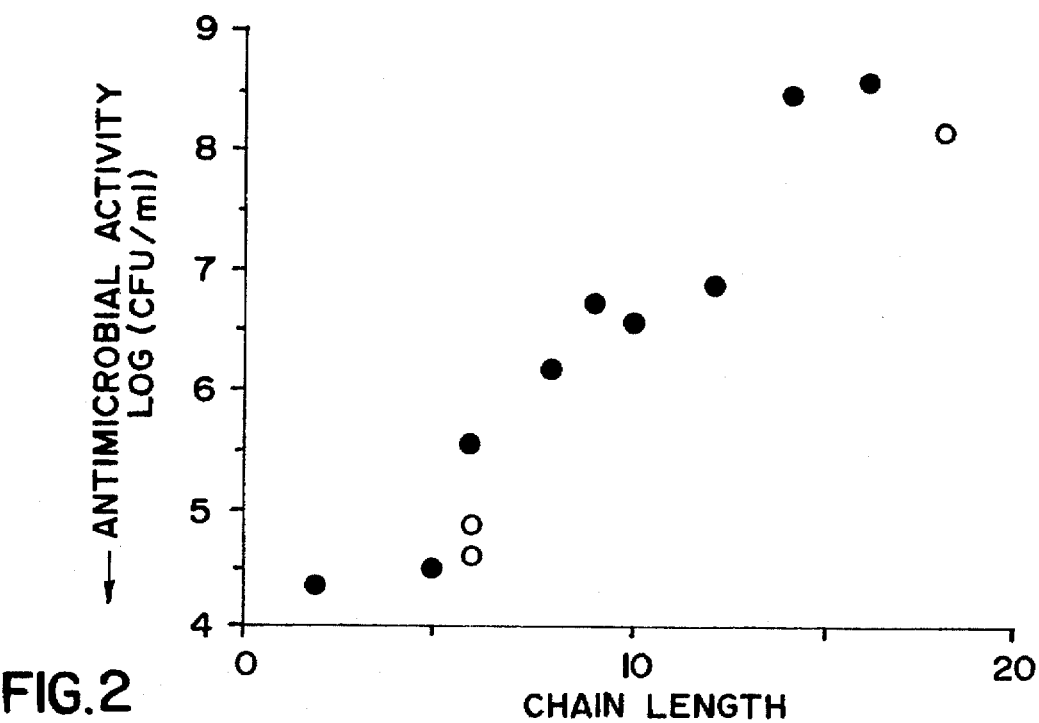
FIG. 2 shows how the antibacterial effect (measured by decrease in log (CFU/ml)) of the compound or compounds of the invention increased with decrease in hydrocarbon chain length.

As can be seen from FIG. 2, shorter chain length resulted in enhanced antibacterial effect. CFU stands for colony forming units and a decrease in CFU/ml is equivalent to greater antibacterial effect.

Example 4

Applicants tested hexanoic acid at various concentrations to determine concentration effect on antibacterial effect. The results are set forth in FIG. 3.

Figure 3:
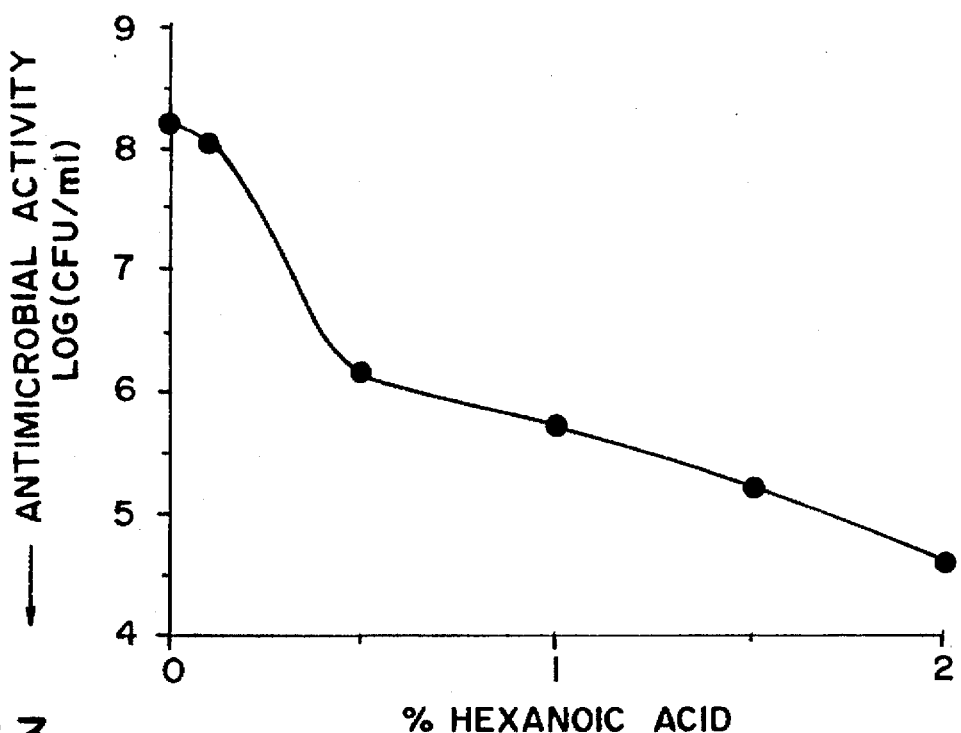
FIG. 3 shows how the antibacterial effect of the compound or compounds of the invention begins immediately and increases with concentration.

As seen in FIG. 3, an effect was seen almost immediately already at concentrations as low as 0.5%.

Example 5

In order to determine pH effect, applicants again tested a compound of the invention (hexanoic acid) at various pH ranges. (pH of Lever 2000 was lowered using hydrochloric acid) and results are seen in FIG. 4.

Figure 4:
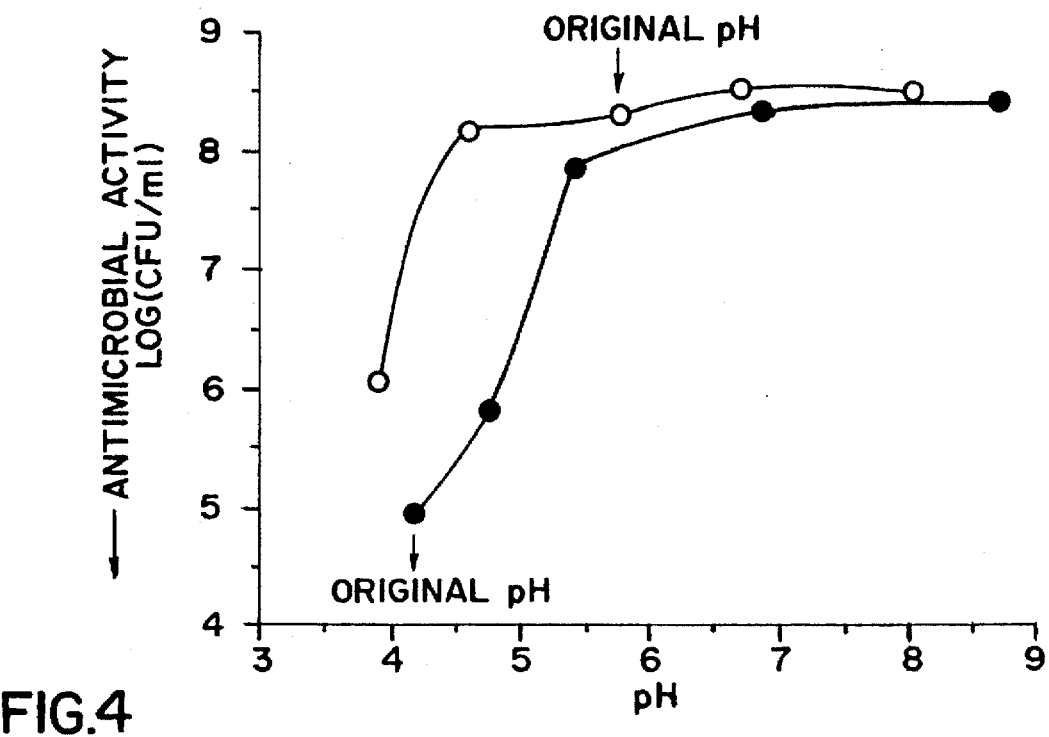
FIG. 4 shows how antibacterial effect of the compound or compounds of the invention increases within the pH range defined by the invention, i.e., 2.5 to 5.5.

As seen in FIG. 4, antibacterial effect is significantly enhanced at pH below 5.

Example 6

In order to show that the invention works in different formulations as well as in formulations which may or may not contain an antibacterial agent, applicants tested the compound or compounds of the invention in various commercial compositions. The results are set forth in FIG. 5.

The various compositions tested are set forth below. The first composition was the composition of Example 1.

Figure 5:
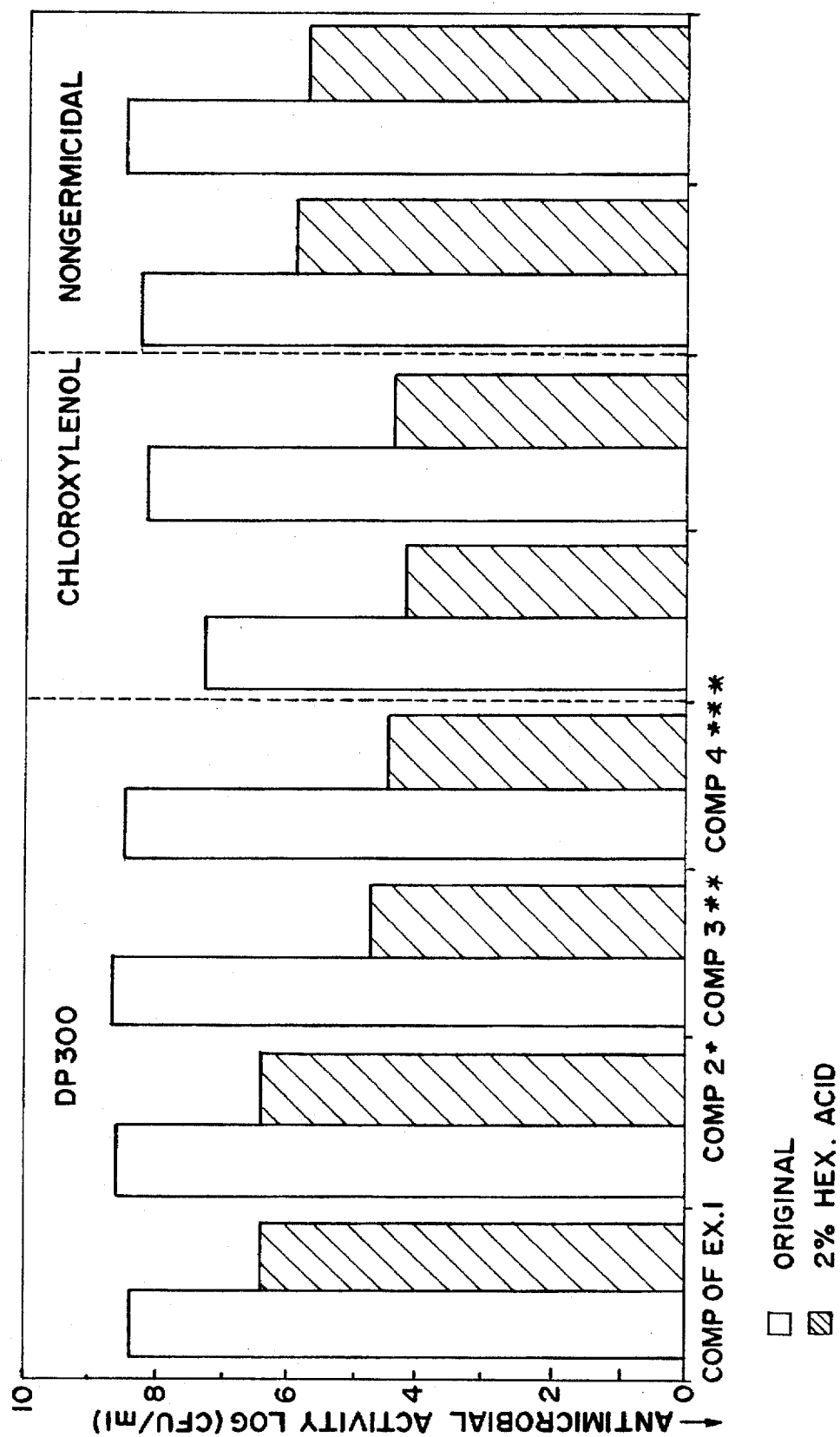
FIG. 5 shows how the antibacterial effect of the compounds or compounds of the invention works in compositions other than those of Example 1. The figure also shows that the enhanced effect is observed in the presence of different antibacterial materials or none at all.

The estimated composition or list of ingredients for various compositions in FIG. 5 (other than Composition of Example 1 ) is set forth below:

| Composition 2* | Estimated % by Weight |
| --- | --- |
| Sodium Laurel Sulfate | 4.5 |
| Sodium Chloride | 2.0 |
| Quaternium - 15 | 1.7 |
| Potassium Cohydrolyzed Collagen | 1.7 |
| Lauryl Polyglucose | 1.6 |
| Cocoamide MEA | 0.4 |
| Triclosan | 0.24 |
| Water | 86.0 |

*Johnson's Liquid Soap No More Germies

Composition 3* (Estimated List of Ingredients)

Triclosan
Water
Sodium $C_{14}$–$C_{16}$ Olefin Sulfonate
Lauramide DEA
Hydrolyzed Silk Protein
cocamidopropyl Betaine
Polyquaternium - 7
Aloe
Glycerin
EDTA
Sodium Chloride Hydantoin
Dyes and Fragrances
* Softsoap Antimicrobial Moisturizing Formula

| Composition 4* (Estimated Ingredients) | Estimated % by wt. |
|---|---|
| Ammonium Lauryl Sulfate | 6.6 |
| Sodium Laureth Sulfate | 5.2 |
| Lauramide DEA | 3.5 |
| Glycerin | 1.5 |
| Isostearamidopropyl Morpholine Lactate | 0.6 |
| Citric Acid | 0.2 |
| Disodium Ricinoleamido MEA Sulfosuccinate | 0.1 |
| Triclosan | 0.2 |
| Water | 80.9 |
| Dyes, EDTA, Hydantoin | |

*Liquid Dial Antibacterial Soap

Clean & Smooth (Estimated Ingredients)

Chloroxylenol
Water
Sodium C14-16 Olefin Sulfonate
Ammonium Lauryl Sulfate
Linoleamide DEA
Cocamide DEA
Cocamidopropyl Betaine
Sodium Chloride
Glycerin
Fragrance
Disodium EDTA
Citric Acid
PEG-45M
Methylchloroisothiazolinone
Methylisothiazolinone
Dyes

Softsoap (Estimated Ingredients)

Chloroxylenol
Water
Sodium C14-16 Olefin Sulfonate
Lauramide DEA
Silk Peptide
Hydrolyzed Silk Protein
Cocamidopropyl Betaine
Poly-Quaternium-7
Aloe Vera Gel
Glycerin
Tetrasodium EDTA
Sodium Chloride
DMDM Hydantoin
Citric Acid
Fragrance
Dyes

Dove Unscented (List of Main Ingredients)

Water
Propylene Glycol
Sodium Isethionate
Sodium Alkylbenzenesulfonate
Sodium Laureth Sulfate
Sodium Cocoyl Isethionate
Sodium Tallow/Coconut Soap
Methyl Paraben
Propyl Paraben
EDTA, EHDP
Fatty Acid
Sulfosuccinate

| Ivory Ultra (Estimated Ingredients) | Estimated % by wt. |
|---|---|
| Sodium Laureth Sulfate | 6.8 |
| Sodium Lauryl Sulfate | 5.0 |
| Lauramide DEA | 2.2 |
| Sodium Sulfate | 2.6 |
| Cocamidopropyl Betaine | 1.8 |
| Sodium Chloride | 0.6 |
| Styrene/Acrylate Copolymer | 0.8 |
| Water | 79.9 |
| Misc. (Octoxynel-9, DMDM Hydanatoin, Tetrasodium EDTA, Citric Acid) | |

As noted from the Figure, the compound of our invention did work effectively in different compositions whether or not a germicide was present.

Example 7

Figure 6:
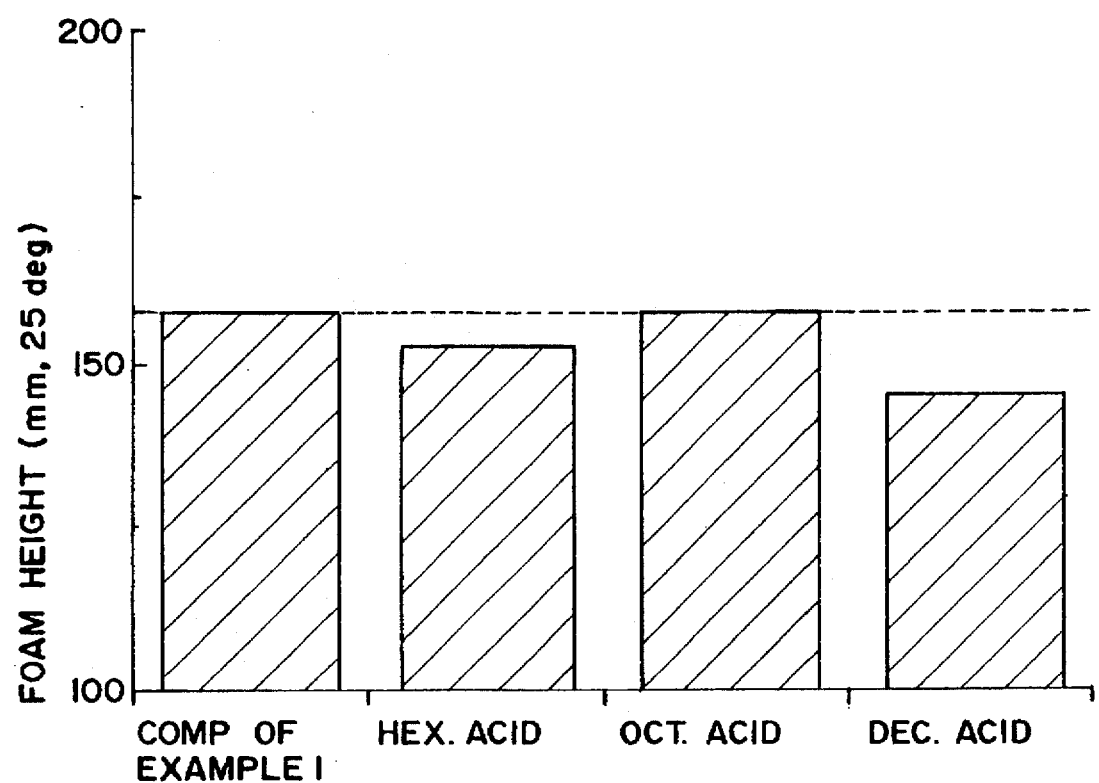
FIG. 6 shows that foam height of the composition is not affected by use of the compound or compounds of the invention.

In order to determine whether the compound or compounds of the invention had a negative effect on foam height, the composition of Example 1 was tested with various fatty acids. Foam height was measured by the method described in ASTM D1173-53 hereby incorporated by reference into the subject application. More particularly, foaming ability of 1% liquid skin cleansing formulations was measured by dripping 200 ml of the solution from Miles pipet onto 50 mL of the solution in a glass cylinder as specified in ASTM D1173-53. Foam height readings were taken after 1 minute and 5 minutes at 25° C. As seen in FIG. 6, foam height remained almost the same.

Example 8

The compound or compounds of the invention may also be used in the following formulations.

| FORMULATION 1 | |
|---|---|
| Component | % by Weight |
| Sodium Isethionate | 3–5% |
| Sodium Alkene Benzene Sulfonate | 1–3% |
| Sodium Laureth Sulfate | 3–5% |
| Sodium Cocoyl Isethionate | 8–12% |
| Sodium Tallow/Coconut Soap | 1–3% |
| Preservative (e.g., Methylparaben) | .1–.5% |
| Sequestrants | .01–.05% |
| Fatty Acid (e.g. Stearic Acid) | 7–10% |
| Sulfosuccinate | 3–5% |
| Water plus minors | to balance |

| FORMULATION 2 | |
|---|---|
| Component | % by Weight |
| Sodium Cocoyl Isethionate | 5–8% |
| Cocamidopropyl Betaine | 5–8% |
| Sulfosuccinate | 2–5% |

-continued

FORMULATION 2

| Component | % by Weight |
| --- | --- |
| Fatty Acid | 6–9% |
| Sodium Isethionate | 1–3% |
| Silicone Emulsion | 3–7% |
| Sequestrant | .01–.05 |
| Water plus minors | to balance |

We claim:

1. A skin cleansing composition consisting essentially of:
   (1) 1% to 15% by wt. acyl isethionate;
   (2) 1% to 15% by wt. of an anonic surfactant other than acyl isethionate;
   (3) 5% to 15% by wt. amphoteric surfactant;
   (4) 1% to 5% by wt. of a pH buffering compound which buffers pH of the composition such that pH is less than 5.0 and which compound is hexanoic acid; and
   (5) balance water.

2. A composition according to claim 1, wherein pH is from about 2.5 to less than 5.0.

3. A composition according to claim 1, wherein pH is from about 3.0 to less than 5.0.

4. A skin cleansing composition consisting essentially of:
   (1) 1% to 15% by wt. acyl isethionate;
   (2) 1% to 15% by wt. of an artionic surfactant other than acyl isethionate;
   (3) 5% to 15% by wt. amphoteric surfactant;
   (4) 1% to 5% by wt. of a pH buffering compound which buffers pH of the composition such that pH is less than 5.0 and which compound is hexanoic acid;
   (5) 0.001% to about 5% by wt. of an antibacterial agent; and
   (6) balance water.

5. A composition according to claim 4, wherein pH is from about 2.5 to less than 5.0.

6. A composition according to claim 4, wherein pH is from about 3.0 to less than 5.0.

* * * * *